United States Patent
Hanash et al.

(10) Patent No.: US 6,677,128 B1
(45) Date of Patent: Jan. 13, 2004

(54) METHOD FOR IDENTIFICATION OF CELLULAR PROTEIN ANTIGENS AND PRESENCE OF ANTIBODIES TO SPECIFIC CELLULAR PROTEIN ANTIGENS IN SERUM

(75) Inventors: Samir M. Hanash, Ann Arbor, MI (US); David Misek, Ann Arbor, MI (US); Robert Hinderer, Flint, MI (US); Latha Prasannan, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/464,840

(22) Filed: Dec. 16, 1999

Related U.S. Application Data

(63) Continuation of application No. PCT/US98/13295, filed on Jun. 26, 1998.
(60) Provisional application No. 60/050,832, filed on Jun. 26, 1997.

(51) Int. Cl.$^7$ ........................ G01N 33/574; G01N 33/53
(52) U.S. Cl. ........................ 435/7.23; 435/7.1; 435/7.2; 436/64
(58) Field of Search ........................ 435/7.1, 7.2, 7.21, 435/7.23, 7.92, 7.93, 7.94, 7.95; 436/64, 63

(56) References Cited

FOREIGN PATENT DOCUMENTS

| WO | WO 92/18535 | 10/1992 |
| WO | WO 94/28021 | 12/1994 |

OTHER PUBLICATIONS

Wollenberg, B. et al., Anti–p53 antibodies in serum of smokers and head and neck cancer patients. Anticancer Res. 17: 413–418, 1997.*
Rainov, N.G. et al. Absence of p53 autoantibodies in sera from glioma patients. Clinical Cancer Research, 1: 775–781, 1995.*
Prasannan, L. et al. Identification of beta–tubulin isoforms as tumor antigens in neuroblastoma. Clinical Cancer Research, 6: 3949–3956, 2000.*
Wurl, P. et al. Detection of p53 autoantibodies in sera of gastric cancer patients and their prognostic relevance. Scand. J. Gastroenterol. 32: 1147–1151, 1997.*
Lawless, B.D. et al, ELISA Assay for Colon Cancer. J. Clinical Laboratory Analysis, 2: 35–38, 1988.*
Fernandez–Madrid, F. et al. Autoimmunity to collagen in human lung cancer. Cancer Res. 56: 121–126, 1996.*
Laurent–Puig, P. et al. Antibodies against p53 protein in serum of patients with benign or malignant pancreatic and biliary diseases. Gut, 36: 455–458, 1995.*
Mudenda, B. et al. The relationship between serum p53 autoantibodies and characteristics of human breast cancer. Br. J. Cancer, 69: 1115–1119, 1994.*
Barbouche, M.R. et al. Prognostic significance of autoantibodies to laminin in the sera of breast cancer patients: A preliminary report. Eur. J. Clin. Chem. Clin. Biochem., 32: 511–514, 1994.*
Miyachi et al., 1978, "Autoantibody to Nuclear Antigen in Proliferating Cells" Journal of Immunology 121:2228–2234.
Bachvaroff, RJ et al., 1980, "Appearance of Cytoskeletal Components on the Surface of Leukemia Cells and of Lymphocytes Transformed by Mitogens and Epstein–Barr Virus" Proc. Natl. Acad. Sci. USA 77:4979–4983.
Crawford, LV et al., 1982, "Detection of Antibodies Against the Cellular Protein p53 in Sera from Patients with Breast Cancer" Int. J. Cancer 30:403–408.
Tan, EM et al., 1987, "PCNA/Cyclin: A Lupus Antigen Connected with DNA Replication" Journal of Rheumatology 14:89–96.
Hanash, SM et al., 1991, "Highly Resolving Two–Dimensional Gels for Protein Sequencing" Proc. Natl. Acad. Sci. USA 88:5709–5713.
Old, LJ, 1998, "New Paths in Human Cancer Serology" J. Exp. Med. 8:1163–1167.

* cited by examiner

Primary Examiner—Mary E. Mosher
(74) Attorney, Agent, or Firm—Baker Botts L.L.P.

(57) ABSTRACT

The present invention relates to a method for identification of cellular protein antigens to which patients with cancer, or patients at risk for cancer, may develop autoantibodies. The method of the invention involves the use of patient derived sera for the identification of the cellular protein antigens using two-dimensional gel electrophoresis followed by Western Blot analysis. The identification of such protein antigens provides novel markers that can be utilized for screening, for diagnostics and prognosis of disease. The invention also provides for the use of the identified protein antigens in immunoassays designed to detect the presence of serum antibodies to the specific protein antigens in sera from individuals that may harbor such antibodies. The invention further relates to the use of the identified antigens as immunogens for stimulation of an immune response in patients expressing such protein antigens. The invention is demonstrated by way of example in which elevated levels of circulating autoantibodies reactive against a tumor specific antigen were identified in sera derived from a lung cancer patient. In addition, elevated levels of circulating autoantibodies reactive against several specific β-tubulin isoforms were detected in the sera of neuroblastoma patients.

5 Claims, 7 Drawing Sheets

SEQUENCE LISTING

<160> NUMBER OF SEQ ID NOS: 9

<210> SEQ ID NO 1
<211> LENGTH: 16
<212> TYPE: PRT
<213> ORGANISM: Homo sapiens

<400> SEQUENCE: 1

Met Arg Glu Ile Val His Ile Gln Ala Gly Gln Cys Gly Asn Gln Ile
 1               5                  10                  15

<210> SEQ ID NO 2
<211> LENGTH: 16
<212> TYPE: PRT
<213> ORGANISM: Homo sapiens

<400> SEQUENCE: 2

Met Arg Glu Ile Val His Leu Gln Ala Gly Gln Cys Gly Asn Gln Ile
 1               5                  10                  15

<210> SEQ ID NO 3
<211> LENGTH: 16
<212> TYPE: PRT
<213> ORGANISM: Homo sapiens

<400> SEQUENCE: 3

Met Arg Glu Cys Ile Ser Ile His Val Gly Gln Ala Gly Val Gln Ile
 1               5                  10                  15

<210> SEQ ID NO 4
<211> LENGTH: 16
<212> TYPE: PRT
<213> ORGANISM: Homo sapiens

<400> SEQUENCE: 4

Met Arg Glu Cys Ile Ser Val His Val Gly Gln Ala Gly Val Gln Met
 1               5                  10                  15

<210> SEQ ID NO 5
<211> LENGTH: 16
<212> TYPE: PRT
<213> ORGANISM: Homo sapiens

<400> SEQUENCE: 5

Glu Glu Gly Cys Val Ser Leu Gln Val Gly Gln Ala Gly Val Gln Ile
 1               5                  10                  15

<210> SEQ ID NO 6
<211> LENGTH: 16
<212> TYPE: PRT
<213> ORGANISM: Homo sapiens

<400> SEQUENCE: 6

Met Arg Leu Ile Val His Ala His Ala Gly Gln Ala Gly Asn Gln Ile
 1               5                  10                  15

<210> SEQ ID NO 7
<211> LENGTH: 16
<212> TYPE: PRT

```
-continued

<213> ORGANISM: Homo sapiens

<400> SEQUENCE: 7

Met Arg Leu Ile Val Asp Ala His Ala Gly Gln Ala Gly Asn Gln Ile
1               5                  10                  15

<210> SEQ ID NO 8
<211> LENGTH: 12
<212> TYPE: PRT
<213> ORGANISM: Homo sapiens

<400> SEQUENCE: 8

Met Arg Glu Ile Val Ser Ile His Val Gly Gln Ala
1               5                  10

<210> SEQ ID NO 9
<211> LENGTH: 12
<212> TYPE: PRT
<213> ORGANISM: Homo sapiens
<220> FEATURE:
<221> NAME/KEY: UNSURE
<222> LOCATION: 4
<223> OTHER INFORMATION: Cysteine or Threonine
<220> FEATURE:
<221> NAME/KEY: UNSURE
<222> LOCATION: 8
<223> OTHER INFORMATION: Glutamine or Proline
<220> FEATURE:
<221> NAME/KEY: UNSURE
<222> LOCATION: 12
<223> OTHER INFORMATION: Cysteine

<400> SEQUENCE: 9

Met Arg Glu Xaa Ile His Ile Xaa Ala Gly Gln Xaa
1               5                  10
```

METHOD FOR IDENTIFICATION OF CELLULAR PROTEIN ANTIGENS AND PRESENCE OF ANTIBODIES TO SPECIFIC CELLULAR PROTEIN ANTIGENS IN SERUM

This is a continuation of copending application PCT/US98/13295 filed Jun. 26, 1998, now PCT publication WO 99/00671, which claims benefit of Ser. No. 60/050,832 filed on Jun. 26, 1997.

INTRODUCTION

The present invention relates to a method for identification of cellular protein antigens to which patients with cancer, or patients at risk for cancer, may develop autoantibodies. The method of the invention involves the use of patient derived sera for the identification of the cellular protein antigens using two-dimensional gel electrophoresis followed by Western Blot analysis. The identification of such protein antigens provides novel markers that can be utilized for screening, for diagnostics and prognosis of disease. The invention also provides for the use of the identified protein antigens in immunoassays designed to detect the presence of serum antibodies to the specific protein antigens in sera from individuals that may harbor such antibodies. The invention further relates to the use of the identified antigens as immunogens for stimulation of an immune response in patients expressing such protein antigens. The invention is demonstrated by way of example in which elevated levels of circulating autoantibodies reactive against a tumor specific antigen were identified in sera derived from a lung cancer patient. In addition, elevated levels of circulating autoantibodies reactive against several specific β-tubulin isoforms were detected in the sera of neuroblastoma patients.

BACKGROUND OF THE INVENTION

Autoantibodies to normal or abnormal cellular proteins are known to be produced by patients in certain diseases such as autoimmune diseases and cardiovascular-related disorders, in some cases even before the disease has produced overt symptoms. However, such autoantibodies have rarely, if ever, been observed in individuals with cancer. Such antibodies to tissue proteins, e.g. p53, may serve as early markers for different types of cancer or for other illnesses. Their detection or the detection of their corresponding antigens in serum or other tissues and body fluids may have utility as indicators of risk for particular types of cancer or for other diseases, as diagnostic markers or as prognostic indicators.

The detection of autoantibodies to cellular antigens and the identification of proteins that have elicited autoantibodies has been accomplished using a variety of approaches. For example, Proliferating Cell Nuclear Antigen (PCNA) was first described as a nuclear antigen which bound antibodies from some patients with lupus erythematosus (Miyachi, K., Fritzler, M. J., and Tan, E. M., 1978, J. Immunol 121:2228–2234). It was subsequently observed that resting lymphocytes did not react with the antibody, in contrast to mitogen stimulated lymphocytes which displayed nuclear staining. This ultimately led to the identification of the protein, designated PCNA which is recognized by this autoantibody in lupus (Tan. E. M., Ogata, K., and Takasaki, Y. 1987, J. Rheumatol., 13:89–96). In some other cases, candidate proteins are singled out and investigated with respect to their ability to induce antibodies in patients, as was investigated for p53 (Crawford, L. V., Firm, D. C. Bulbrook, R. D., 1984, Int J Cancer 30:403–408). In addition, a technique called SEREX relies on serological analysis of recombinant cDNA expression libraries to identify tumor antigens (Old, L., et al. 1998, J. Exp. Med. 187:1163–1167). Thus, many approaches have been followed to search for proteins against which autoantibodies may be produced.

The combination of two different electrophoresis methods (so called "two dimensional" or "2D"-electrophoresis) has been widely utilized to separate proteins in complex mixtures such as tissues or body fluids. The first electrophoresis step generally separates proteins based on their charge. The second electrophoresis step generally separates proteins based on their molecular weight. The use of high resolution two-dimensional electrophoresis allows the simultaneous separation of up to several thousand individual proteins, providing an overall protein map of the protein mixture analyzed. The separated proteins can be visualized in the gel by means of staining with a variety of staining compounds including Coomassie blue or silver. Alternatively, mixtures containing isotopically labeled proteins such as with $^{25}S$ methionine, can be visualized by means of autoradiography.

Methods have been developed for the identification of protein(s) that react with a specific antibody among a large number of proteins separated by two-dimensional electrophoresis. The technique of Western blotting can readily reveal the protein with which the antibody reacts if the protein is sufficiently abundant and the antibody is sufficiently specific and with a sufficiently high titer, i.e., high affinity and avidity. The use of whole sera that may contain unknown antibodies against unknown protein antigens present in tumors or precancerous lesions for Western blotting of two dimensional gels has not been reported. Such technology may theoretically be complicated by a large measure of nonspecific reactivity, making it difficult to interpret results. Thus, the methods of the present invention, using Western blotting of two-dimensional gel electrophoresis of complex protein mixtures for the identification of novel antigens for which autoantibodies are present in sera of patients with tumors or with precancerous lesions, is novel.

SUMMARY OF THE INVENTION

It is an object of the present invention to provide a procedure for the identification of cellular protein antigens and for the detection of antibodies to specific cellular protein antigens in the serum of patients with cancer or with precancerous lesions. The identification of such protein antigens provides novel markers that can be used for screening, diagnostics and prognosis of disease.

The invention comprises separating antigen-containing protein mixtures by two-dimensional gel electrophoresis followed by transfer of the separated proteins onto a membrane. Specific antigens in the protein mixture are detected by treatment of the membrane with a patient's sera followed by detection of specifically bound antibody by use of a second labeled antibody which specifically binds the first antibody. Separated protein antigens are considered disease specific antigens if they show prominence in the presence of sera suspected of harboring autoantibodies compared to control sera. The source of proteins for two-dimensional analysis includes unfractionated tumors, isolated cancer cells or tumor infiltrating cells or cultured cell lines or subcellular protein fractions such as secreted proteins, membrane proteins, cytosolic or nuclear proteins.

The present invention also relates to the use of the identified protein antigens in immunoassays designed to detect the presence of serum antibodies to the specific protein antigens. Such immunoassays can be utilized for screening, for diagnostics and prognosis of disease. In accordance with the invention, measurement of antibody levels in a patient's sample can be used for the early diagnosis of diseases such as cancer. Moreover, the monitoring of serum antibody levels can be used prognostically to stage progression of the disease.

Additionally, the present invention further relates to the use of the identified protein antigens as immunogens for stimulation of an host immune response against the tumor cells. It is expected that such an approach can be used as a method for inhibiting tumor cell growth or facilitating tumor cell killing in individuals with specific cancers.

In a specific embodiment of the invention described herein, circulating autoantibodies reactive against specific β-tubulin isoforms, and their cleavage products, were detected in the sera of patients with neuroblastoma. The finding that β-tubulin isoforms are immunogenic in neuroblastoma patients provides a basis for development of diagnostic methods for neuroblastoma and other cancers in which these β-tubulin isoforms are expressed, as well as a means for monitoring prognosis of various therapeutic treatments for the disease. In addition the discovery that specific β-tubulin isoforms are expressed in tumor cells provides a method for use of specific β-tubulin isoforms as immunogens for stimulation of an immune response against the tumor cells.

DETAILED DESCRIPTION OF THE INVENTION

Figure 1A:
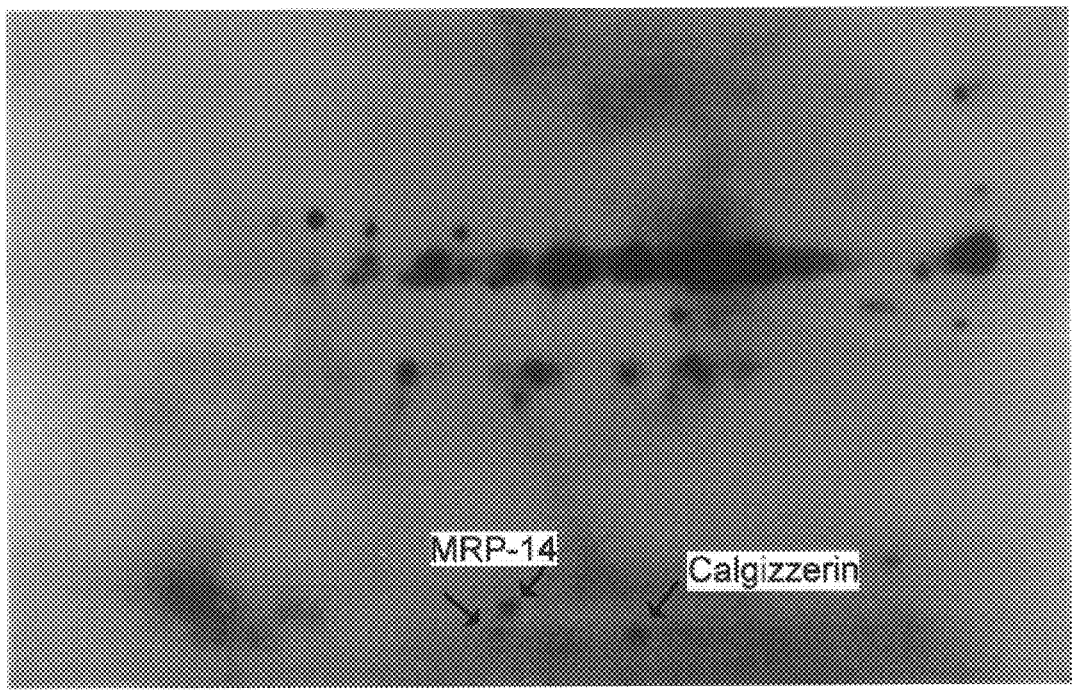
FIG. 1A. Western blots of a lung adenocarcinoma treated with a serum from a patient with lung adenocarcinoma tumor.

The present invention achieves a highly desirable objective, namely the identification of novel protein antigens for which individuals with, or at risk for different types of cancer, carry autoantibodies against tumor cell protein antigens. Such protein antigens can in turn be purified and utilized to screen a patient's serum for the presence of circulating antibodies to such antigens, by means of sensitive and rapid immunoadsorbent assays or by other procedures. The invention also relates to using the novel protein antigens to immunize patients suffering from diseases characterized by the expression of the identified protein antigens. Stimulation of an immunological response to such antigens, is intended to elicit a more effective attack of tumor cells; such as inter alia inhibiting tumor cell growth or facilitating the killing of tumor cells.

Specifically, the method for identifying novel protein antigens, to which a subject with cancer produces autoantibodies, comprises the following steps:

(a) extracting proteins from a sample of cells;

(b) separating the extracted proteins by two-dimensional electrophoresis;

(c) transferring the proteins separated by two-dimensional electrophoresis to a membrane;

(d) incubating the membrane with antiserum from a subject known to have the cancer;

(e) detecting the proteins to which autoantibodies in the patients serum have bound; and (f) comparing the proteins to which antibodies in the subject's serum sample bind, to the proteins to which antibodies in a control serum sample bind, wherein those proteins bound by antibodies in the subject s serum but not the control serum are identified as proteins to which a subject with cancer produces autoantibodies.

A wide variety of protein mixtures that may contain antigens against which autoantibodies are present in serum can be prepared and separated into individual proteins by means of two-dimensional electrophoresis. Whole cell extracts or body fluids can be analyzed for proteins which have elicited autoantibodies. Alternatively, subsets of proteins such as secreted proteins, nuclear proteins or membrane proteins can be subjected to two-dimensional electrophoresis and analyzed separately for proteins which have elicited autoantibodies so as to increase the abundance of such proteins in the mixture. Preparative loads consisting of several milligrams of proteins in a mixture can also be applied to electrophoretic gels to increase the amounts of proteins which have elicited autoantibodies.

The particular advantage of the present invention is that no prior knowledge concerning the nature of the antigen is necessary. Autoantibodies to multiple antigens can be detected simultaneously through the use of a two-dimensional separation procedure. Additionally, the pattern of reactivity of a serum with a particular set of proteins in the two dimensional gel patterns, may be diagnostic of a particular cancer or indicative of a risk for a particular cancer.

The present invention is based on the discovery that serum from an individual that contains autoantibodies, such as a patient with cancer of the lung or neuroblastoma, can be used to identity protein antigens expressed in cells of a particular tissue, such as for example, cells of a tumor, or in a representative cell type, to which the patient has autoantibodies. As described herein, serum from neuroblastoma patients contained antibodies which were immunospecific for β-tubulin isoforms.

Identification of Disease Associated Protein Antigens

The present invention provides a method for identifying cellular protein antigens to which patients with cancer may develop autoantibodies. The method is validated by the use of serum from individuals with cancer and from controls without cancer. A body fluid which may contain autoantibodies, such as serum, is obtained from a patient known to have a particular cancer. A similar body fluid containing antibodies is obtained from a control subject that does not have cancer. In addition, tumor tissue as well as normal tissue to be used as a control is obtained. Additionally or alternatively, tumor tissues from other patients with the same disease and control tissues from other normal controls can be utilized. It is also not necessary to utilize primary tissues; cells grown in culture may provide appropriate substitutes for tumor tissues or controls. In addition, protein subsets from such tissues or such cells in culture may be prepared. Such subsets may include secreted proteins, nuclear proteins, membrane proteins or other subcellular fractions.

Two dimensional gel electrophoresis is used to separate proteins in complex mixtures of proteins. Electrophoresis in the first dimension generally separates proteins based on charge, while electrophoresis in the second dimension, referred to as SDS PAGE, separates proteins based on size.

Prior to two-dimensional gel electrophoresis, aliquots of whole tissues, or cells are solubilized using any one of a variety of solubilization cocktails known to those of skill in the art. For example, tissue can be solubilized by addition of lysis buffer consisting of (per liter) 8 M urea, 20 ml of Nonidet P-40 surfactant. 20 ml of ampholytes (pH 3.5–10), 20 ml of 2-mercaptoethanol, and 0.2 mM of phenylmethylsulfonyl fluoride (PMSF) in distilled deionized water.

Because isoelectric focusing is sensitive to charge modification, it is important to minimize protein alterations (e.g., proteolysis, deamidation of glutamine and asparagine, oxidation of cystine to cystic acid, carbamylation) that can result from improper sample preparation. Thus, once solibilized, samples should be stored frozen at −80° C. for short periods (<1 month) to limit significant protein modification.

Approximately 30 µl aliquots containing 70 ug of protein may be loaded on individual gels. Prepared protein samples are loaded onto electrophoretic gels for isoelectric focusing separation in the first dimension which separates proteins based on charge. A number of first dimension gel preparations may be utilized including tube gels for carrier ampholyte-based separations, or gel strips for immobilized gradient based separations. After first dimension separation, proteins are transferred onto the second dimension gel, following an equilibration procedure and separated using SDS PAGE which separates proteins based on molecular weight. Multiple gels can be prepared from individual samples.

Methods of two dimensional electrophoresis are known to those skilled in the art. For example, carrier ampholyte based two dimensional gel electrophoresis can be done as previously described (Strahier et al. Journal of Clinical Investigation, 85:200–207, 1990). In most cases aliquots are immediately applied onto isoelectric focusing gels (IEF). First-dimension gels contain 50 ml of ampholytes per liter (pH 3.5–10). Generally, isoelectric focusing is done at 1,200 V for 10 h and 1,500 V for the last 2 h. 20 gels are generally run simultaneously. For the second-dimension separation by SDS PAGE, an acrylamide gradient of 11.4–14.0 g/ml can be used. If desired, protein spots in gels may be visualized by the silver-staining technique of Merril et al. (Merril et al, Science, 211:1437–1438. 1961).

Alternatively, immobilized pH gradient (IPG) two dimensional gels may be used (Hanash S. M., et al., 1991, Proc. Natl. Acad. Sci., USA 88:5709–5713). Samples are prepared using lysis buffer as discussed above. For first dimension separation an immobilized pH gradient covering the separation range of pH 4–10 is used. The second dimension is the same as for the carrier ampholyte gels described above. IPG gels are prepared using derivatives of acrylamide having carboxyl or tertiary amino groups with specific pK values. A linear pH gradient is prepared from a dense, acidic solution and a light, basic solution using a two-chamber microgradient former. The pH gradient is stabilized during polymerization of the Immobiline acrylamide-bisacrylamide matrix by a co-linear gradient of glycerol. Formulations of buffering Immobiline mixtures with titrating Immobiline for the pH limit solutions for narrow pH gradients (1 pH unit) or for broad pH gradients (>1 pH unit, up to 6 pH units) have been published (Gianazza et al, Electrophoresis 6:113 (1985) and LKB application Note 324 (1984)).

The second dimension separates proteins on the basis of molecular weight in an SDS gel. An 11.5 to 14% (2.6% cross-linking) acrylamide gradient provides effective separation of proteins having a mass of from 10,000 to 100.000 Da. Proteins outside this range may be less well resolved. Proteins with molecular weight less than 10,000 Da electrophorese close to the dye front and are less well resolved.

Following separation the proteins are transferred from the two dimensional gels onto membranes commonly used for Western blotting. The techniques of Western blotting and subsequent visualization of proteins are also well known in the art (Sambrook et al, "Molecular Cloning, A Laboratory Manual", $2^{nd}$ Edition, Volume 3, 1989, Cold Spring Harbor). The standard procedures may be used, or the procedures may be modified as known in the art for identification of proteins of particular types, such as highly basic or acidic or lipid soluble, etc. (See for example, Ausubel, et al., 1989, Current Protocols in Molecular Biology, Green Publishing Associates and Wiley Interscience, N.Y.). The patient and control sera are diluted to various concentrations, e.g., one volume of serum to 100 volumes of buffer, prior to being utilized in an incubation step, as in the procedure of Western blot analysis. Non-specific binding may be minimized by preclearing the serum prior to the incubation step. A second antibody specific for the first antibody is utilized in the procedure of Western blot analysis to visualize proteins that reacted with the first antibody.

It is expected that some proteins will be visualized as spots as a result of nonspecific reactivity with antibodies in the serum. Spots corresponding to proteins that have elicited specific autoantibodies are distinguishable from nonspecific spots based on their presence in Western Blots prepared with patients' sera compared to control sera, and/or the presence of a spot in the disease tissues or cell lines or extracts compared to control tissues, cell lines or extracts.

The protein spots, in two dimensional gels of the same protein source used for Western blots are visualized using a staining procedure or by autoradiography. Spots in the gels that match the spots of interest in Western blots are identified by means of an overlay or a matching procedure between the gels and the blots. Once the spots that contain proteins that may have elicited autoantibodies are identified in two-dimensional gels, the protein can be extracted from the two-dimensional gels and utilized for a structural characterization and/or for making antibodies against such protein. The amino acid sequence of the protein can be derived by direct sequencing with an automated amino acid sequencer.

Once a protein of interest has been identified, it may be isolated and purified by standard methods including chromatography (e.g., ion exchange, affinity, and sizing column chromatography), centrifugation, differential solubility, or by any standard technique for purification of proteins. Such purified protein can be used in immunoassays designed to detect the presence of autoantibodies in a subject's serum, or alternatively, such protein preparations may be used for immunization as described infra.

The present invention is demonstrated by way of example wherein elevated levels of circulating autoantibodies reactive against several specific β-tubulin isoforms and their cleavage products were detected in the sera of neuroblastoma patients. The detection and/or quantitative measurement of β-tubulin isoforms or their cleavage products in serum or other body fluids can be used in screening of subjects who are at risk for neuroblastoma or other disorders in which β-tubulin isoforms are expressed. Additionally, autoantibodies to the specific β-tubulin isoforms were not detected in neuroblastoma patients being treated, or in remission from the disease, indicating that measurement of autoantibodies can be used prognostically to stage the progression of the disease. Thus, the specific subtypes of tubulin autoantibodies may have diagnostic, prognostic, or therapeutic significance.

Immunoassays

In accordance with the invention, measurement of autoantibodies reactive against an identified tumor specific protein antigen can be used for the early diagnosis of diseases such as cancer. Moreover, the monitoring of autoantibody levels can be used prognostically to stage the progression of the disease. The detection of autoantibodies in a sample from a patient can be accomplished by any of a number of methods. Such methods include immunoassays which include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, to name but a few.

Such an immunoassay is carried out by a method comprising contacting a serum sample derived from a subject with a sample containing the protein antigen under conditions such that specific antigen-antibody binding can occur, and detecting or measuring the amount of any immunospecific binding by the autoantibody. In a specific aspect, such binding of autoantibody by tissue sections, for example, can be used to detect the presence of autoantibody wherein the detection of autoantibody is an indication of a diseased condition. The levels of autoantibodies in a sample are compared to the levels present in an analogous sample from a portion of the body or from a subject not having the disorder.

The immunoassays of the invention are not limited to those designed for detection of autoantibodies in a subject's serum, but also include, immunoassays for detecting expression of the identified protein antigens in a subject's sample. To this end, purified protein antigen can be used to produce antibodies that can be used in accordance with the invention. For example, the protein antigens identified by the method of the invention can be prepared in preparative gels, eluted from the gels, and used as immunogens for the production of antibodies which immunospecifically bind such an immunogen. The antibodies are made by methods known to those skilled in the art. Such antibodies include but are not limited to polyclonal, monoclonal, chimeric, single chain, Fab fragments, and an Fab expression library.

Antibodies can be used in assays, such as the immunoassays listed above, to detect, prognose, diagnose, or monitor cancer in an individual, or monitor the treatment thereof. In particular, such an immunoassay is carried out by a method comprising contacting a sample derived from a subject with an antibody under conditions such that immunospecific binding can occur, and detecting or measuring the amount of any immunospecific binding by the antibody. In addition, reagents other than antibodies, such as, for example, nucleic acid molecules, polypeptides or chemical compounds that specifically bind to β-tubulin isoforms, can be used in assays to detect the expression of β-tubulin isoforms.

In a specific aspect, such binding of antibody by tissue sections, can be used to detect expression of the protein wherein the expression of the protein is an indication of a diseased condition. The levels of expressed proteins are compared to levels relative to that present in an analogous sample from a portion of the body or from a subject not having the disorder.

Immunization

The identification of autoantibodies to novel protein antigens associated with particular cancers provides a basis for immunotherapy of the disease. The patient may be immunized with the protein antigens to elicit an immune response which facilitates killing of tumor cells or inhibiting tumor cell growth. The protein antigens can be prepared using the methods described above for purification of proteins.

In an embodiment of the invention an immunogen comprising a purified protein antigen to which a patient cancer has developed autoantibodies, is used to elicit an immune response. For administration, the protein antigen may be formulated with a suitable adjuvant in order to enhance the immunological response to the protein antigen. Suitable adjuvants include, but are not limited to mineral gels, e.g.

aluminum hydroxide, surface active substances such as lysolecithin, pluronic polyols, polyanions, peptides, oil emulsions, and potentially useful human adjuvants such as BCG (*bacilli Calmett-Guerin*) and (*Corynebacterium parvum*). Many methods may be used to introduce the formulations derived above; including but not limited to oral, intradermal, intramuscular, intraperitoneal, intravenous, and subutaneous.

The results presented in the Examples infra are discussed below. In particular, the data presented in Section 7 demonstrate that specific β-tubulin isoforms are expressed in the tumors of subjects having neuroblastoma. Knowledge of the antigenic nature of β-tubulin isoforms in cancer can be used in devising therapeutic strategies in the form of immunotherapy directed against cancer using β-tubulin isoforms or peptides as an intermediate target to stimulate an immune response against the tumor or in the form of gene therapy using genes that encode all or part of β-tubulin isoforms as an intermediate target. Additionally, β-tubulin III differs from other forms of tubulin by a short sequence at the C-terminal end. Thus peptides encompassing this sequence may be utilized as an immunogen to elicit antibodies specifically reactive to against tumors that express β-tubulin III.

EXAMPLE: DETECTION OF A TUMOR SPECIFIC ANTIGEN USING SERUM ISOLATED FROM A PATIENT HAVING CANCER

The method of the present invention was applied to patients with lung cancer for identification of tumor specific antigens. One such experiment is described below. An aliquot of a lung adenocarcinoma tumor was solubilized in a urea cocktail, as described above, and 40 micrograms of solubilized protein was loaded onto a carrier ampholyte based (pH 3–8) tube gel and subjected to isoelectric focusing in the first dimension for 12,000 volt hours (700V×16h and 1000V×2h). The first-dimension tube gel was loaded onto a cassette containing the second dimension gel, after an equilibration step. Electrophoresis in the second dimension using SDS PAGE, was done until the tracking dye present in the equilibration buffer reached the opposite end of the second dimension gel, in relation to the first dimension gel. Following electrophoresis the separated proteins were transferred onto a nitrocellulose membrane. The membrane was preincubated with a blocking buffer and subsequently incubated with serum obtained from a patient with lung adenocarcinoma at a dilution of 1/100 (diluted in Tris-buffered-saline (TBS);0.01% Tween 20; 1.8 gm/100 ml non-fat dry milk), for 1 hr at room temperature. After three washes with a buffer solution, the membrane was incubated for 1 hr with a sheep anti-human antibody (available from Amersham). Reactive proteins were revealed with luminol.

Figure 1B:
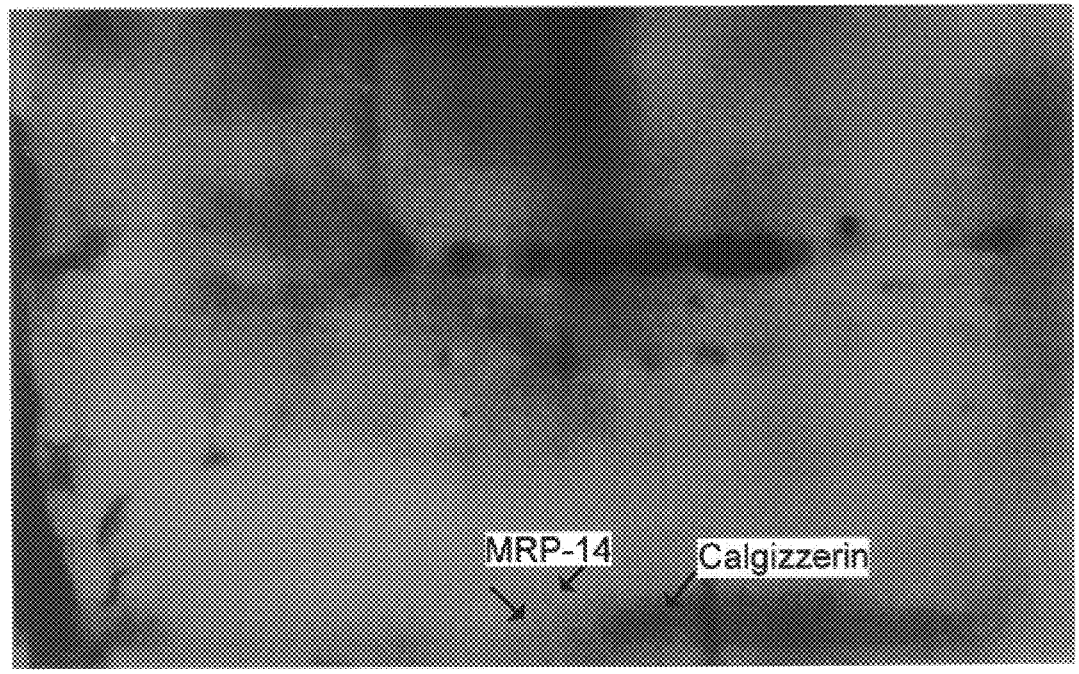
FIG. 1B. A normal lung treated with serum from a patient with lung adenocarcinoma.

A candidate protein in the tumor for which an antibody was present in the patient's serum is shown in FIG. 1A. As indicated in FIG. 1B, the protein spot was not detectable in a blot of normal lung proteins which was incubated with the patient's serum.

EXAMPLE: DETECTION OF ANTIBODIES SPECIFIC FOR β-TUBULIN ISOFORMS IN THE SERA OF SUBJECTS WITH NEUROBLASTOMA

Using the method of the present invention, sera from subjects with neuroblastoma were screened for reactivity against tumor proteins. The sera samples from the neuroblastoma patients were found to be reactive against a set of neuroblastoma specific proteins identified as β-tubulin isoforms and their cleavage products.

Materials and Methods

Sera were obtained from patients with neuroblastoma as well as from patients with other tumor types including cancer of the lung, esophagus, sarcomas and Wilms tumors. Different Western blots were prepared using the different tumors or the neuroblastoma cell line SY5Y as sources for solubilized proteins. An aliquot of SY5Y proteins was solubilized in a urea cocktail as described above and 40 micrograms of solubilized protein was loaded onto a carrier ampholyted base (pH 3.8) tube gel and separated by isoelectric focusing in the first dimension for 12,000 volt hours (700V×16 h followed by 1000V×2 h). The first-dimension tube gel was loaded onto a cassette containing the second dimension gel, after an equilibration step. Electrophoresis in the second dimension using SDS PAGE was done until the tracking dye present in the equilibration buffer reached the opposite end of the second dimension gel, in relation to the first dimension gel.

Following electrophoresis the separated proteins were transferred on to a polyvinylideme flouride (PVDF) membrane (Millipore). The membrane was preincubated with a blocking buffer and subsequently incubated with serum obtained from the same patient with neuroblastoma whose tumor was being analyzed. The serum, which was diluted 1:100 in the buffer solution (Tris-buffered-saline containing 0.01% Tween20 and 1.8 gm/100 ml non-fat dry milk), was incubated with the filter for 1 hr at room temperature. After three washes with the buffer solution, the membrane was incubated for 1 hr with a rabbit anti-human IgG antibody (available from Amersham). Reactive proteins were revealed with luminol. A set of coalesced protein spots labeled LP1, were identified as containing β-tubulin isoforms for which an autoantibody was present in the patient's serum.

Figure 2:
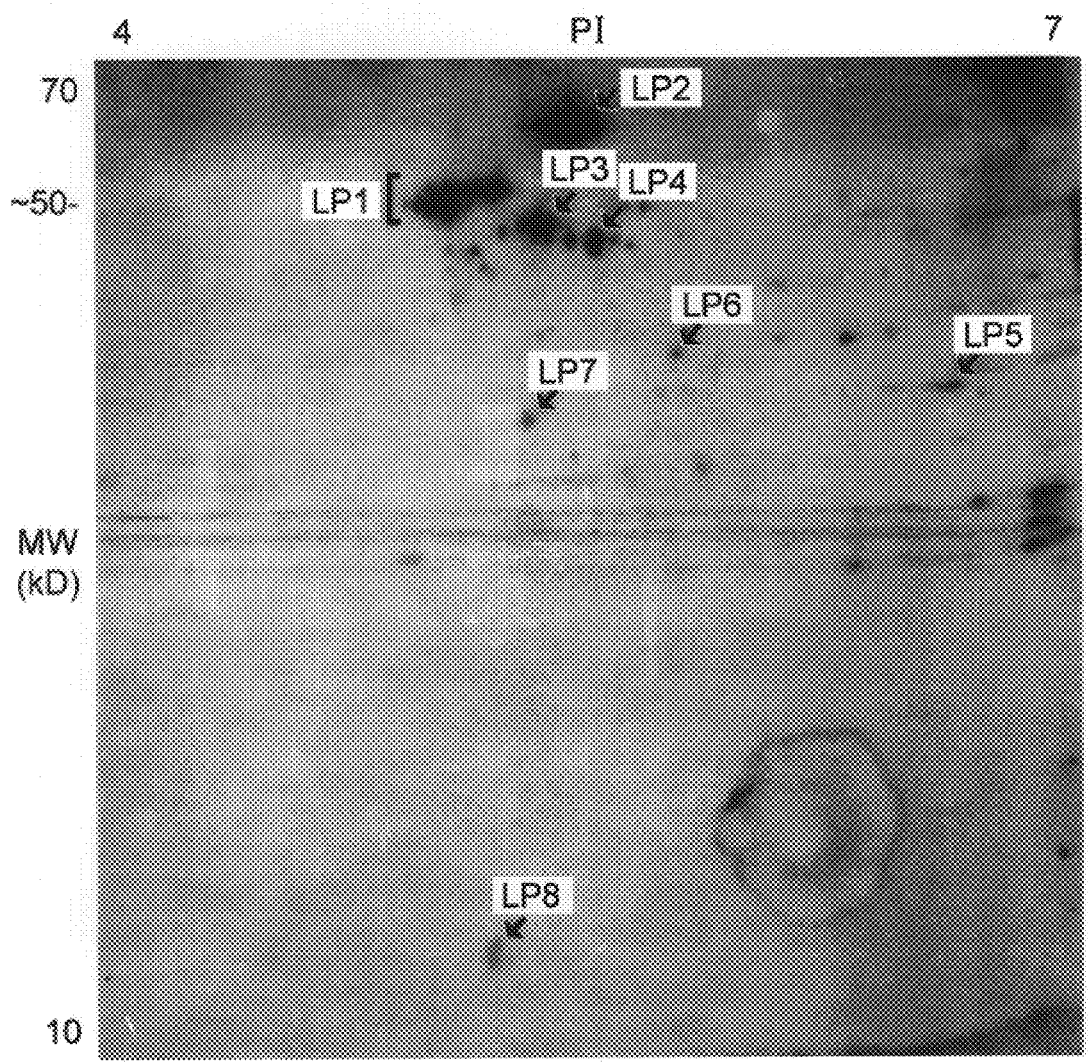
FIG. 2. Western blot of a two-dimensional gel separation of a primary neuroblastoma SY5Y lysate treated with the serum from a newly diagnosed patient with neuroblastoma. An aliquot of SY5Y proteins was solubilized in a urea cocktail and 40 micrograms of solubilized protein was loaded onto a carrier ampholyte base (pH 3.8) tube gel and separated in the first dimension for 12,000 volt hours. The first-dimension tube gel was loaded onto a cassette containing the second dimension gel, after an equilibration step. Electrophoresis in the second dimension was performed until the tracking dye present in the equilibration buffer reached the opposite end of the second dimension gel, in relation to the first dimension gel. Following electrophoresis, the separated proteins were transferred on to a polyvinylideme flouride (PVDF) membrane. The membrane was preincubated with a blocking buffer and subsequently incubated with serum obtained from the same patient with neuroblastoma whose tumor was analyzed. The serum was utilized at a dilution of 1:100, for 1 hr at room temperature. After three washes with a buffer solution, the membrane was incubated for 1 hr with a rabbit anti-human IgG antibody. Reactive proteins were revealed with luminol. A set of coalesced protein spots labeled as LP1 was identified as containing β-tubulin isoforms for which an antibody was present in the patient's serum. This set was not detectable in a similar blot which was incubated with the serum of patients with other types of cancer or with the serum of normal individuals.
Figure 3:
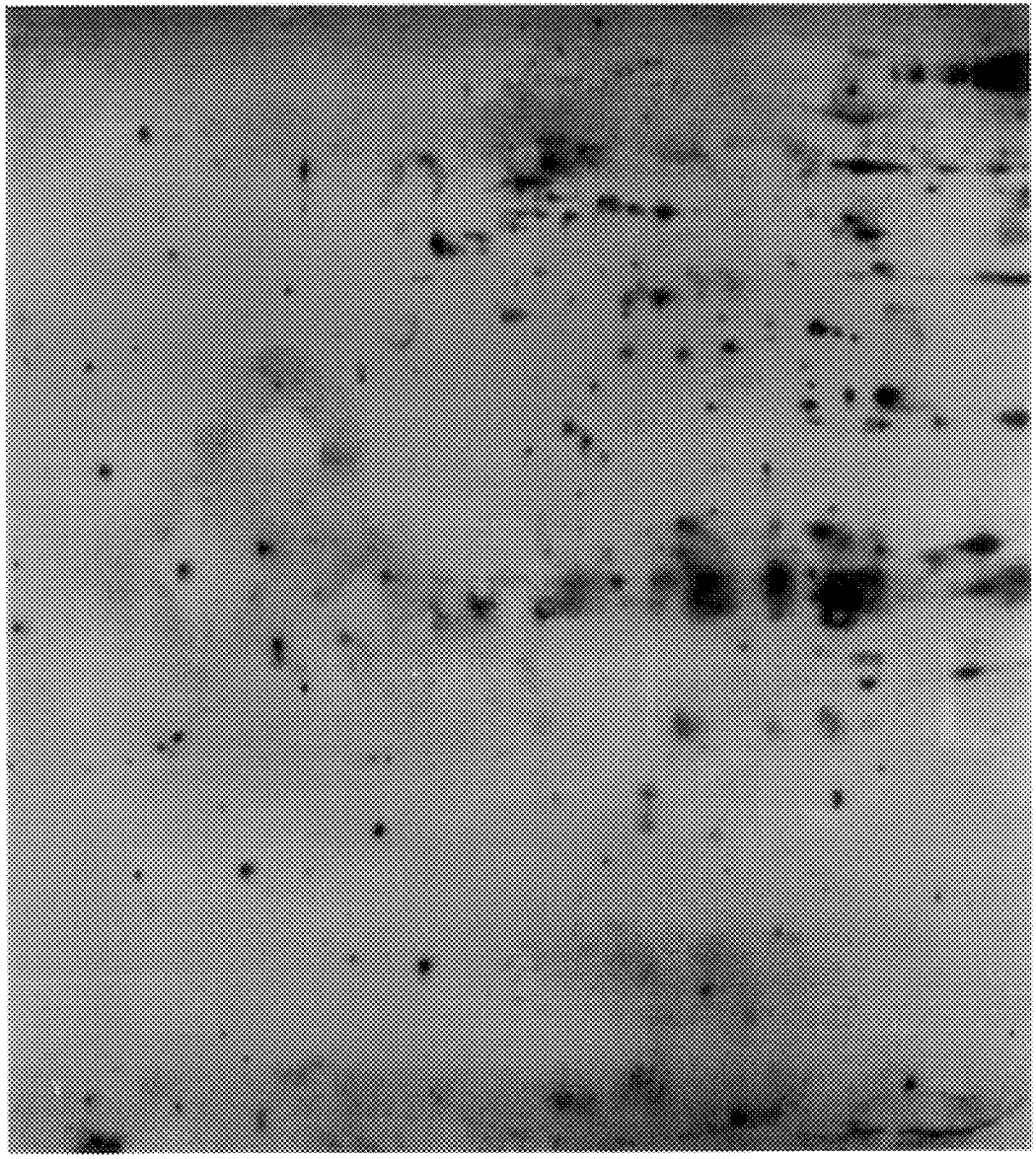
FIG. 3. Western blot of two-dimensional gel separation of neuroblastoma protein lysate treated with the serum of a newly diagnosed patient with Wilms tumor. The conditions for the Western blot are as described in FIG. 2. There is a lack of reactivity in the region of LP1.
Figure 5:
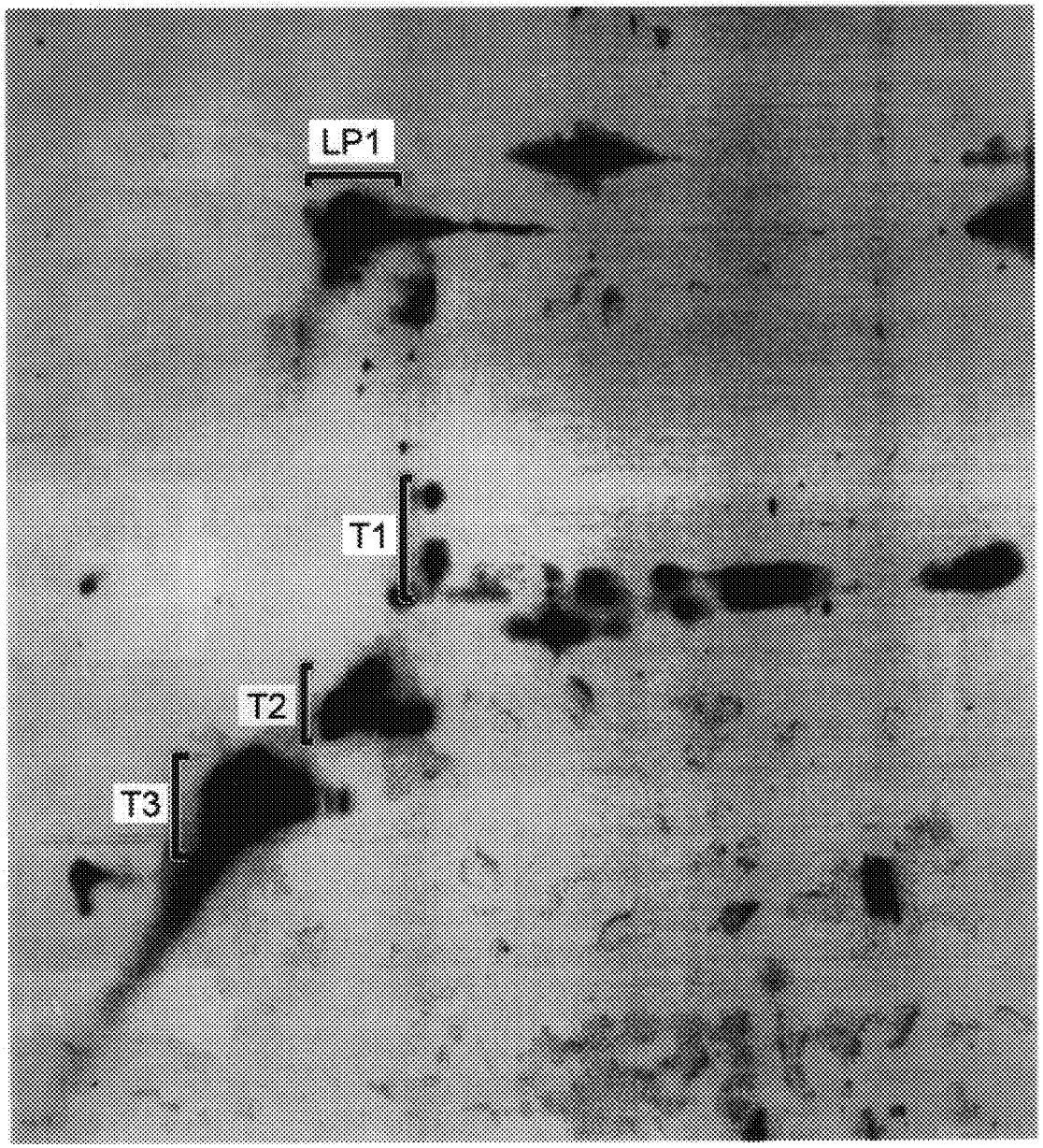

Several immunoreactive spots occurred in Western blots of neuroblastoma patient sera. These spots were absent in Western blots of other tumors or in Western blots of neuroblastoma tumors that were treated with control sera (FIGS. 2 and 3). The set of neighboring immunoreactive proteins, designated LP1, observed in blots in which the second antibody was directed against IgG or IgM (FIGS. 2 and 3, respectively) was identified in two-dimensional separations of the same tumor extracts, in which total proteins were visualized by staining with silver or Coomassie blue, based on their isoelectric point (pI) and MW following a matching process (FIG. 5). This protein constellation was identified as containing tubulin β-isoforms types I, II and III as determined by amino acid sequencing and reactivity with known antibodies to these tubulin β-isoforms.

For amino acid sequencing, several blots of neuroblastoma tumor proteins were prepared and stained with Coomasie Blue. The coalesced spots, designated LP1, which occurred in the position of the immunoreactive constellation of spots were excised from four contiguous areas of neuroblastoma blots stained with Coomassie Blue and the N-terminal amino acid sequence was determined for each excised protein spot. The N-terminal amino acid sequences were compared to the known N-terminal sequences of the β-tubulin isoforms.

The reported N-terminal sequences for the β-tubulin isoforms are as follows:

| | | M.W. | P.I. | |
|---|---|---|---|---|
| TBB1 | MREIVHIQAGQCGNQI | 49759 | 4.75 | (SEQ ID NO:1) |
| TBB3 | MREIVHIQAGQCGNQI | 50517 | 4.86 | (SEQ ID NO:1) |
| TBB2 | MREIVHLQAGQCGNQI | 49831 | 4.79 | (SEQ ID NO:2) |
| TBB5 | MREIVHLQAGQCGNQI | 49631 | 4.81 | (SEQ ID NO:2) |
| TBA1 | MRECISIHVGQAGVQI | 50157 | 5.02 | (SEQ ID NO:3) |
| TBA4 | MRECISVHVGQAGVQM | 49924 | 4.95 | (SEQ ID NO:4) |

Figure 7:
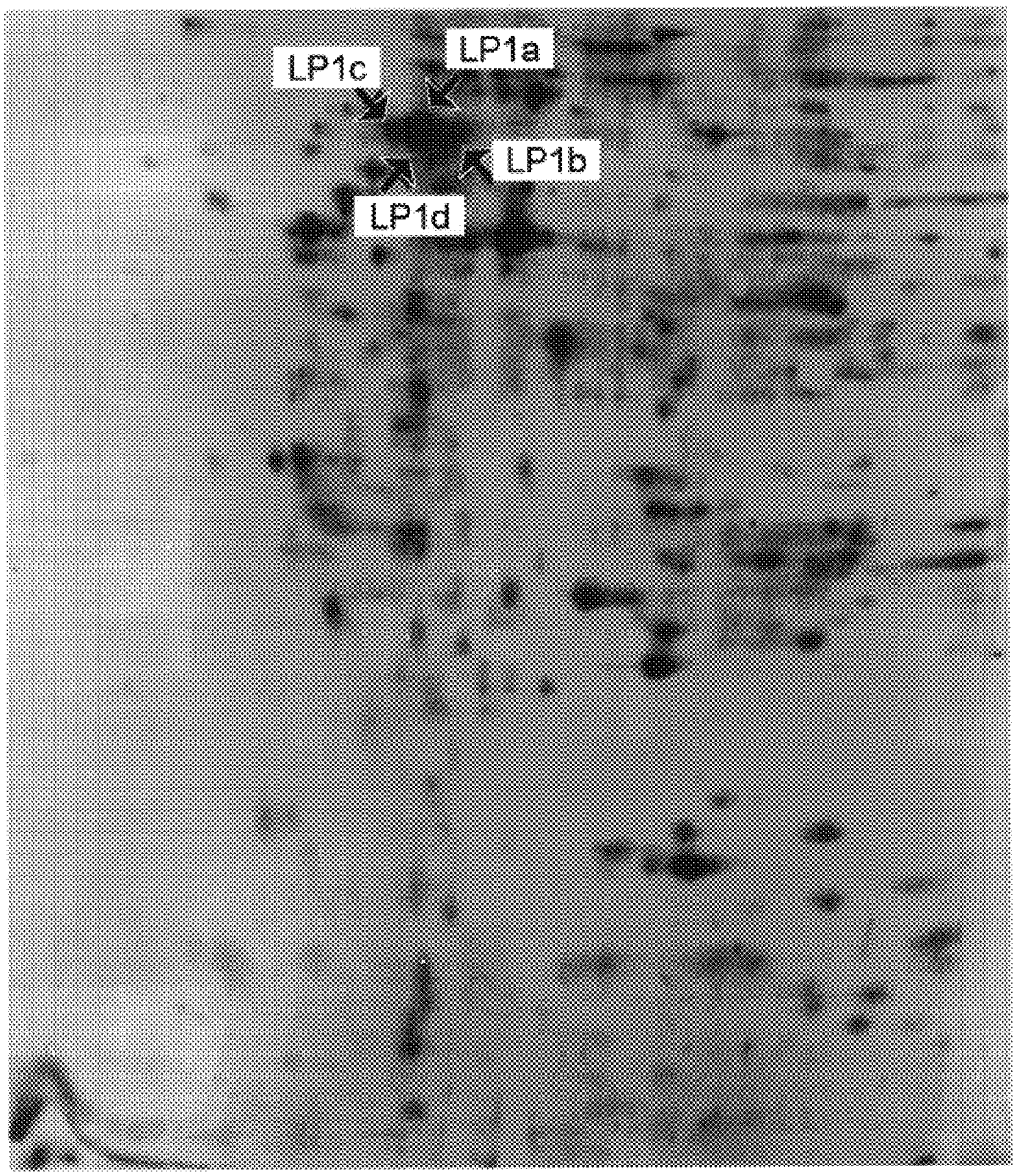
FIG. 7. Coomassie Blue stained blot of Sy5Y proteins. Similar blots were used to cut out LP1 spots for amino acid sequencing.

The spots designated LP1a to LP1d in FIG. 7 were excised and the amino terminal sequence of each protein was determined. The amino acid sequences were as follows:

I. LP1a major-MREIVHIQAGQCGNQI (SEQ ID NO:1)

minor-EEGCVSLQVGQAGVQI (SEQ ID NO:5)

The major sequence of LP1 is that of tubulin isoform TBB1 or TBB3, the minor is TBB2 or TBB5. TBB1 and TBB3 have the same N-terminus, but differ at C-terminus. There were some minor signals as well in some cycles. TBB2 and TBB5 have L instead of I in position 7. There was some L observed in this cycle. However it may have come from an unrelated sequence along with the other minor residues.

II. LP1b major-MRECISIHVGQAGVQI (SEQ ID NO:3)

minor-MRLIVHAHAGQAGNQI (SEQ ID NO:6)

minor-MRLIVDAHAGQAGNQI (SEQ ID NO:7)

The major sequence is of LP1b is that of tubulin isoform TBA1 and the minor sequence is that of tubulin isoform TBB1 and/or TBB3.

III. LP1c major-MREIVHIQAGQCGNQI (SEQ ID NO:1)

minor-MREIVHLQAGQCGNQI (SEQ ID NO:2)

The major sequence of LP1c is that of tubulin isoform TBB1 and/or TBB3 with possibly some TBB5 and/or TBB2 tubulin isoforms present (Lin #7).

Figure 6:
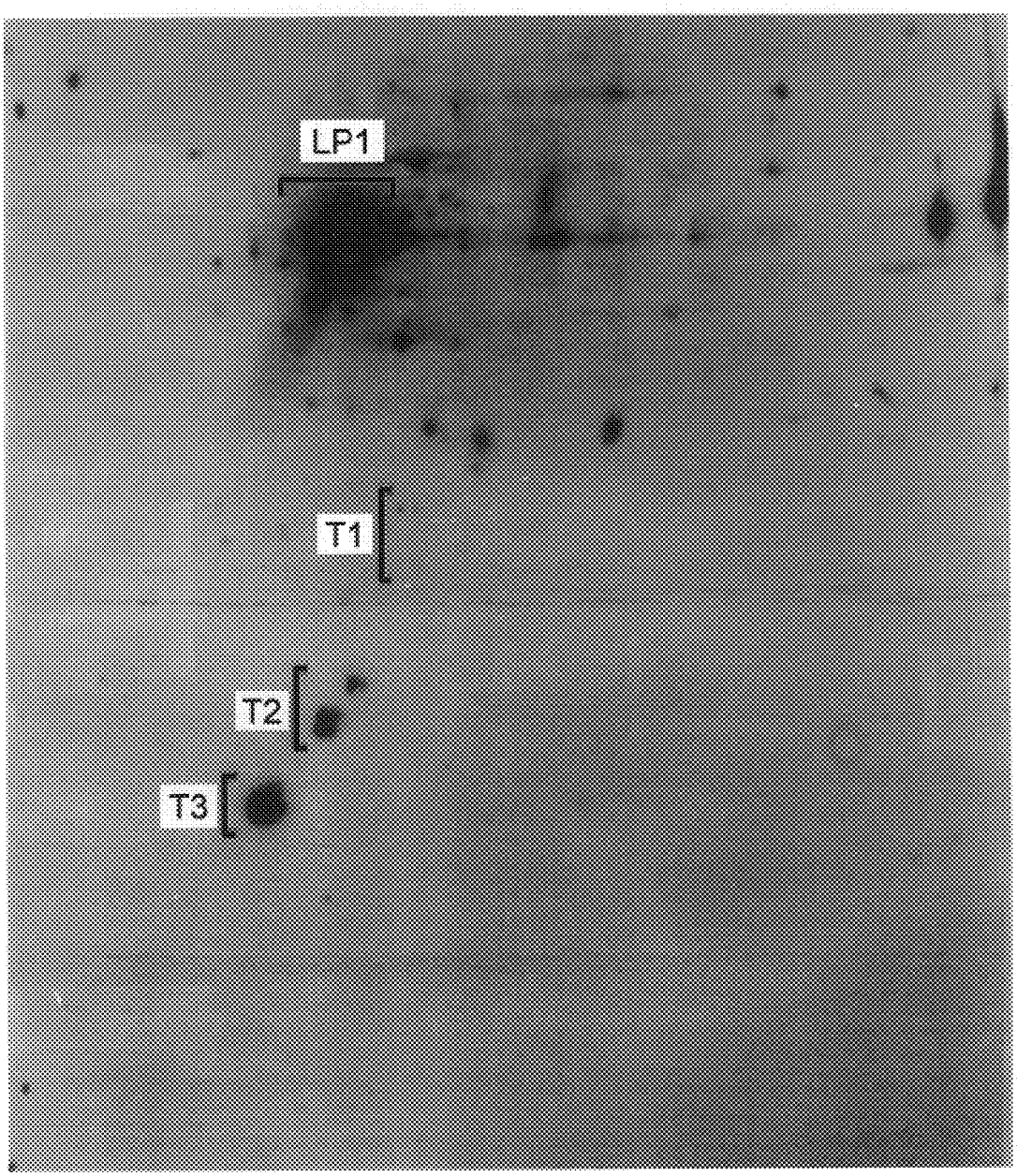
FIG. 6. Western blot of Sy5Y proteins treated with a monoclonal antibody that reacts with tubulin BIII. Reactive spots are identified as LP1, and T1–T3.

IV. LP1d major-MREIVSIHVGQA (SEQ ID NO: 8)

minor-MREXaaIHIXaaAGQXaa (SEQ ID NO:9), wherein the first Xaa refers to the presence of a C or T residue; the second Xaa refers to the presence of a Q or P residue; and the third Xaa refers to the presence of a C residue. The major sequence of LP1d is tubulin isoform TBB1 and/or TBB3 with a minor amount of TBA1 tubulin isoform detected.

β-tubulin isoforms types I and II and type III were found to be expressed at high level in neuroblastoma tumors and the SY5Y based on Western blot analysis of neuroblastoma tumor proteins separated by two dimensional gel electrophoresis, using isoform specific tubulin beta antibodies (FIGS. 5, 6).

Figure 4:
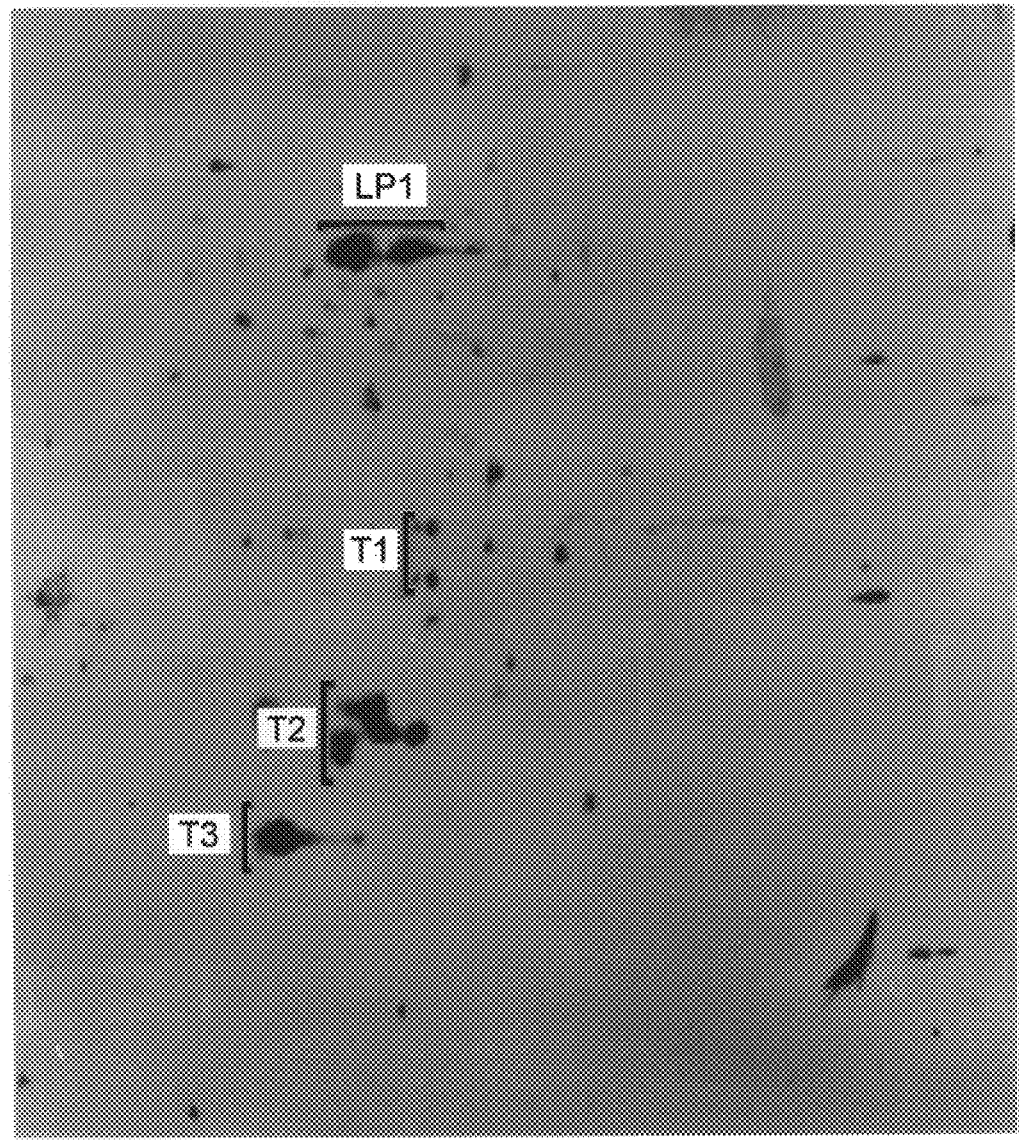
FIG. 4. Western blot of two-dimensional gel separation of SY5Y protein lysate treated with the serum of a newly diagnosed patient with neuroblastoma. The conditions for the Western Blot are as described in FIG. 2 with the exception that the membranes were incubated for 1 hr with a rabbit anti-human IgM antibody. Reactive proteins were revealed with luminol. A set of lower molecular weight proteins indicated as T1, T2 and T3 were identified as containing β-tubulin isoforms. This set was not detectable in a similar blot which was incubated with control sera FIG. 5. Western blot of SY5Y proteins treated with a monoclonal antibody that reacts with β-tubulin BI and BII. Reactive spots are identified as LP1, and T1–T3.

Another set of immunoreactive proteins observed in Western blots of neuroblastoma tumors and Sy5Y cell line, in which the second antibody was directed against IgM were identified as cleavage products of β-tubulin isoforms, based on their reactivity with β-tubulin isoform specific antibodies (FIG. 4). This set of neighboring proteins was also identified in two-dimensional separations of the same tumor extracts, in which proteins were visualized by staining with silver or Coomassie blue, based on their isoelectric point (pI) and molecular weight (MW) following a matching process (FIG. 7).

Cleavage products of tubulin beta isoforms types I and II and type III were found to be expressed at high level in neuroblastoma tumors based on Western blot analysis of neuroblastoma tumor and SY5Y proteins separated by two dimensional gel electrophoresis using isoform specific tubulin beta antibodies (FIGS. 4, 5 and 6).

Results

For identification of neuroblastoma protein antigens and the presence of serum autoantibodies to neuroblastoma tumor proteins, sera from patients with neuroblastoma was used to screen for reactivity against tumor proteins separated by the technique of high resolution two-dimensional electrophoresis. Tumor proteins were transferred following their two-dimensional separation onto a polyvinylideme flouride (PVDF) membrane and incubated with serum from newly diagnosed patients with neuroblastoma using the technique of Western blotting (FIGS. 2 and 4). Sera from patients with other types of cancer and from normal individuals were similarly utilized as controls (FIG. 3).

Proteins which reacted with antibodies present in serum were detected based on the visualization of a spot following incubation with a second antibody directed against the first antibody. Antibody specificity was determined by means of comparisons of Western blots of different tumor types reacted with different neuroblastoma patient sera, with Western blots reacted with control sera.

Several immunoreactive spots that were found in Western blots of neuroblastoma tumors and a neuroblastoma cell line that were incubated with sera from neuroblastoma patients were absent in Western blots of other tumors or in neuroblastoma Western blots that were treated with control sera. One set of neuroblastoma immunoreactive proteins was localized in two-dimensional separations of neuroblastoma proteins in which proteins were revealed by staining with silver or Coomassie Blue. Localization was based on a matching process which took into account protein isoelectric point (pI) and molecular weight. Following elution from the membrane, he immunoreactive set of protein antigens were identified as β-tubulin isoforms as determined by amino acid sequencing, mass spectrometry and reactivity with known antibodies to tubulin beta isoforms. β-tubulin isoforms were found to be expressed at high level in neuroblastoma tumors based on Western blot analysis of neuroblastoma tumor proteins separated by two dimensional gel electrophoresis, which were reacted with isoform specific β-tubulin antibodies. Another set of immunoreactive proteins were similarly identified as cleavage products of tubulin beta isoforms. Thus, patients with neuroblastoma appear to make autoantibodies to β-tubulin isoforms or to their cleavage products. Interestingly, serum taken from neuroblastoma patients either in remission or being treated for their disease fail to contain autoantibodies reactive against β-tubulins. The identification of tubulin beta isoforms as immunogenic in cancer provides a basis for the development of diagnostic and screening tests for cancers in which these isoforms are expressed and for the development of novel tubulin based strategies for cancer therapy.

Once proteins that have elicited autoantibodies are identified, it becomes possible to produce them in large quantities through recombinant DNA technology or other enrichment or purification procedures. Specific antibodies and antisera can be produced against these proteins or against synthetic peptides which match the derived sequence of the protein(s) of interest.

The present invention is not to be limited in scope by the embodiments disclosed in the examples which are intended as an illustration of one aspect of the invention, and any

What is claimed is:

1. A method for diagnosing neuroblastoma in a subject comprising:
   (a) obtaining a serum sample from a subject; and
   (b) detecting the presence of autoantibodies specific for a β-tubulin isoform,
   wherein the presence of autoantibodies indicates the presence of neuroblastoma.

2. A method for prognosis of neuroblastoma in a subject, comprising:
   (a) obtaining a serum sample from a subject; and
   (b) measuring the level of autoantibodies specific for a β-tubulin isoform,
   wherein the absence of a detectable level of autoantibodies specific for β-tubulin isoform correlates with a good prognosis.

3. The method of claim 1 or 2 wherein the presence of autoantibodies in the sample is measured by an immunoassay.

4. The method of claim 3 wherein the immunoassay comprises:
   (a) immobilizing a β-tubulin isoform onto a membrane or substrate;
   (b) contacting the membrane or substrate with a subject's serum sample; and
   (c) detecting the presence of autoantibodies specific for the β-tubulin isoform in the subject's serum sample.

5. The method of claim 1 or 2 wherein the β-tubulin isoform is selected from the group consisting of:
   (i) a β-tubulin isoform having the amino acid sequence of SEQ ID NO:1;
   (ii) a β-tubulin isoform having the amino acid sequence of SEQ ID NO:2;
   (iii) a β-tubulin isoform having the amino acid sequence of SEQ ID NO:3;
   (iv) a β-tubulin isoform having the amino acid sequence of SEQ ID NO:4;
   (v) a β-tubulin isoform having the amino acid sequence of SEQ ID NO:5;
   (vi) a β-tubulin isoform having the amino acid sequence of SEQ ID NO:6;
   (vii) a β-tubulin isoform having the amino acid sequence of SEQ ID NO:7;
   (viii) a β-tubulin isoform having the amino acid sequence of SEQ ID NO:8; and
   (ix) a β-tubulin isoform having the amino acid sequence of SEQ ID NO:9.

* * * * *